United States Patent [19]
Clinkenbeard

[11] Patent Number: 5,004,696
[45] Date of Patent: Apr. 2, 1991

[54] AUTOMATIC TOTAL REDUCERS MONITORING AND ADJUSTMENT SYSTEM

[75] Inventor: Jack L. Clinkenbeard, Anaheim, Calif.

[73] Assignee: Ashland Oil, Inc., Russell, Ky.

[21] Appl. No.: 172,682

[22] Filed: Mar. 24, 1988

[51] Int. Cl.$^5$ .................... C01N 21/00; C01N 31/00
[52] U.S. Cl. .................................... 436/51; 436/52; 436/119; 436/120; 436/123; 436/163; 436/165; 422/63
[58] Field of Search ............... 436/119, 120, 123, 50, 436/51, 163, 52; 422/63; 356/36

[56] References Cited

U.S. PATENT DOCUMENTS

| | | | |
|---|---|---|---|
| 2,124,307 | 7/1938 | Mewborne et al. | 23/230 |
| 2,413,261 | 12/1946 | Stackhouse | 23/232 |
| 3,635,820 | 1/1972 | Urban | 210/61 |
| 3,702,235 | 11/1972 | Fallgatter | 23/230 R |
| 3,992,109 | 11/1976 | Bock | 356/181 |
| 4,026,665 | 5/1977 | Mansfield et al. | 23/230 PC |
| 4,174,202 | 11/1979 | Simpson | 23/230 R |
| 4,270,924 | 6/1981 | Crooke et al. | 23/230 B |
| 4,355,998 | 10/1982 | Verbeek et al. | 23/230 R |
| 4,409,336 | 10/1983 | Oita | 436/123 |
| 4,416,786 | 11/1983 | Knorre et al. | 210/746 |
| 4,554,255 | 11/1985 | Ishii et al. | 436/102 |
| 4,555,491 | 11/1985 | Spurlin et al. | 436/120 |
| 4,575,433 | 11/1986 | Spurlin et al. | 252/700 |

OTHER PUBLICATIONS

APHA Standard Methods-13th Method, 1971, pp. 336-338.
"Chemical Analysis for Thiosulfate and Sulfite in Industrial Wastewater-Sep. 1975," Modified Los Angeles County Sanitation District Procedure.
Olin Water Services Total Reducer Titration Analytical Method (printed Nov. 1985).
Hach Hardness Monitor Model 120 product brochure (no date).
Technicon Monitor 650 product brochure (dated Jan. 1984).
Dionex Series No. 8000 Analyzer product brochure (copyright 1984).

*Primary Examiner*—Robert J. Warden
*Assistant Examiner*—David Redding
*Attorney, Agent, or Firm*—Marc C. Pawl

[57] ABSTRACT

A process and apparatus for automatically monitoring or adjusting, or both, the concentration of total reducers (i.e. reduced sulfur-containing constituents which consume iodine) in an aqueous medium (e.g. waste water stream) whereby the time period for iodine titration of an untreated sample of the aqueous medium is automatically measured and this time measurement is automatically translated into an output signal to either a monitoring means or a process adjustment means (e.g. oxidant chemical feed pump) or both.

10 Claims, 3 Drawing Sheets

SAMPLE CELL END POINT SENSING

SAMPLE CELL LEVEL SENSING

AUTOMATIC TOTAL REDUCERS MONITORING AND ADJUSTMENT SYSTEM

BACKGROUND OF THE INVENTION

1. Field of the Invention

The present invention relates to a process and apparatus for monitoring or adjusting, or both, the concentration of total reducers in a water medium.

2. Brief Description of the Prior Art

Oil refineries and other industrial complexes often have effluent waste water streams which contain high concentrations of reduced sulfur compounds including sulfides ($S^{-2}$), thiosulfates ($S_2O_3^{-2}$) and sulfites ($SO_3^{-2}$). Such waste water streams must be chemically treated or placed in bioponds before being discharged into public waterways or going to public owned treatment works in order to comply with discharge permits. One common method of treating these sulfur-bearing waste water streams is by adding to the stream an oxidizing chemical such as hydrogen peroxide, chlorine dioxide, potassium permanganate, chlorine gas, sodium hypochlorite or ozone.

In the past, the required amount of oxidizing chemical to be added to the waste water stream was determined by first analyzing a batch sample of the stream. This batch analysis was then related to the flow rate of the stream and the final treated pollutant level desired. The chemical oxidant feed rate was manually adjusted following every such determination.

The standard laboratory analysis for measuring the aggregate concentration of reduced sulfur compounds was a batch iodometric analysis. This analysis is sometimes referred to as a Total Reducers analysis. Such an analysis attempts to determine the aggregate concentration of all of the reduced sulfur compounds and other chemicals which consume iodine. One particular known batch method involves first adding four chemical reagents (i.e. a pH 5.0-5.5 phosphate buffer, a methyl red indicator solution, hydrochloric acid and a starch indicator solution) to a waste water sample. Then, an iodine solution is titrated into the mixture of the waste water sample and chemical reagents until a color change occurs. The reduced sulfur components in the water sample quantitatively react with the iodine titrant under certain acidic conditions (i.e. pH 5.0-5.5). When all of these reduced species are consumed by this reaction, the iodine starts to react with the starch indicator to form a blue complex signaling the end point of the titration. Upon reaching the endpoint, the total amount of titrated iodine is measured and the concentration of total reducers as milligrams of thiosulfate as sulfur or sulfite as sulfur per liter of water is calculated therefrom.

Typical batch analysis procedures are illustrated in APHA Standard Methods 13th Edition, 1971, pages 337 and 338 and the Modified Los Angeles County Sanitation District Method September 1985 and Olin Water Services Analytical Method for Total Reducers Titration (dated November 1985). All three of these procedures are incorporated herein by reference in their entireties.

Until the present invention, no one had attempted to automate any standard batch iodometric analysis so that the total reducers level in a waste water stream could be continuously monitored. Furthermore, no Total Reducers analytical system has been used to automatically control process adjustment means (e.g. oxidant chemical feed pumps).

Technicon Industrial Systems of Terrytown, New York, has manufactured an on-line hydrogen sulfide monitor (Model 650) for the intermittent (once per hour) detection of hydrogen sulfide ($H_2S$) content in an aqueous stream using a colorimetric methodology of detection. However, this Technicon monitor does not measure thiosulfate and other total reducer constituents in an aqueous stream.

Dionex Corporation of Sunnyvale, Calif., manufactures an on-line monitor (Model 8000) which is capable of detecting the concentration of the individual anion and cation components in an aqueous stream with ion exchange methodology. By this method, a small sample of a water stream is passed through an ion exchange column and the various ionic constituents are loosely attached by the ionic charge to the resin. During regeneration of the resin column, the various ionic contituents are eluted in a specific order and may be qualitatively identified and quantitatively measured by ion chromatography.

Both the Technicon and Dionex systems are very sensitive to the presence of suspended solids and oils in the aqueous sample being tested. Accordingly, both use a submicron filter to pretreat the aqueous samples being tested. This pretreatment of the sample may easily introduce errors into the analysis procedure by removing a portion of the chemical constituents being analyzed. Accordingly, these Technicon and Dionex monitors are best used for analyzing fresh water and laboratory water. Neither is well suited for waste water analysis. Finally, neither monitor is designed to provide an output signal based on an monitored combination of a variable flow rate and a total reducers concentration to a process control means (e.g. chemical feed pump) which controls the level of the oxidant reactant feed into a waste water stream.

Accordingly, there is a need in the water treatment industry for an automated Total Reducers analytical system which can provide a very frequent analysis of total reducers concentration in a water stream without prefiltering or other preconditioning means. Furthermore, there is a need in this industry for an automated Total Reducers analytical system, when coupled with a flow monitoring means, that can automatically control a process adjustment means (e.g. oxidant chemical feed pump), especially when a variable flow rate of water stream is involved. The present invention is a solution to both of these needs.

BRIEF SUMMARY OF THE INVENTION

The present invention, therefore, is directed to a process for monitoring or adjusting, or both, the concentration of total reducer constituents in an aqueous medium, comprising the steps of:

(1) adding a predetermined aliquot of total reducers-containing water to a sample cell, said sample cell equipped with means for transmitting light of variable intensities through the filled sample cell and means for sensing the presence or absence of said light transmission after passing through the filled sample cell;

(2) adding to said filled sample cell predetermined amounts of a pH 5.0-5.5 buffer reagent, optional methyl red indicator, optional hydrochloric acid and a starch indicator;

(3) activating said light transmission means in said sample cell in order to send light of sufficient intensity to said light sensing means through the filled sample cell;

(4) then titrating an iodine solution into the sample cell at a predetermined rate of addition while sensing the presence of said light transmission in said cell;

(5) measuring the time taken from the start of the iodine titration until the absence of said light sensing through said filled cell is detected;

(6) translating this time measurement into either the concentration of total reducer constituents in said water medium or into the amount of an oxidant chemical to be fed into said water medium or both; and (7) based on said translation, sending either a first output signal to at least one monitoring means (e.g. a visual monitor, a printer or a recorder) or a second output signal to at least one process adjustment means (e.g. an oxidant chemical feed pump) located on said water medium, whereby said concentration of total reducer constituents in said water medium is adjusted, or sending both signals.

Furthermore, the present invention is directed to an apparatus for monitoring or adjusting, or both, the concentration of total reducer constituents in a water medium; said apparatus comprising:

(a) a sample cell capable of containing a predetermined aliquot of a total reducers-containing water sample and predetermined amounts of chemical reagents and equipped with means for transmitting light of variable intensity through a filled sample cell and means for sensing the presence or absence of light transmission through said filled cell;

(b) means for dispensing the predetermined aliquot of total reducers-containing water into said sample cell;

(c) means for dispensing the predetermined amounts of chemical reagents into the sample cell, said chemical reagents comprising a pH 5.0–5.5 buffer, optional methyl red indicator, optional hydrochloric acid and a starch indicator;

(d) means for titrating an iodine solution into said sample cell at a predetermined rate of addition until said light transmission is not sensed by light sensing means;

(e) means for measuring the period of time from the start of said iodine titration to the point of detection of said absence of light sensing; and (f) means for translating said time period into a determination of either the concentration of total reducer constituents in said water sample or into the amount of an oxidant chemical to be fed into said water medium, or both, and said translation means capable of providing a first or second output signal or both signals based on said translation, said first output signal being sent to at least one monitoring means and said second output signal being sent to at least one process adjustment means whereby the concentration of total reducer constituents in said water medium is adjusted.

DETAILED DESCRIPTION

Figure 1:
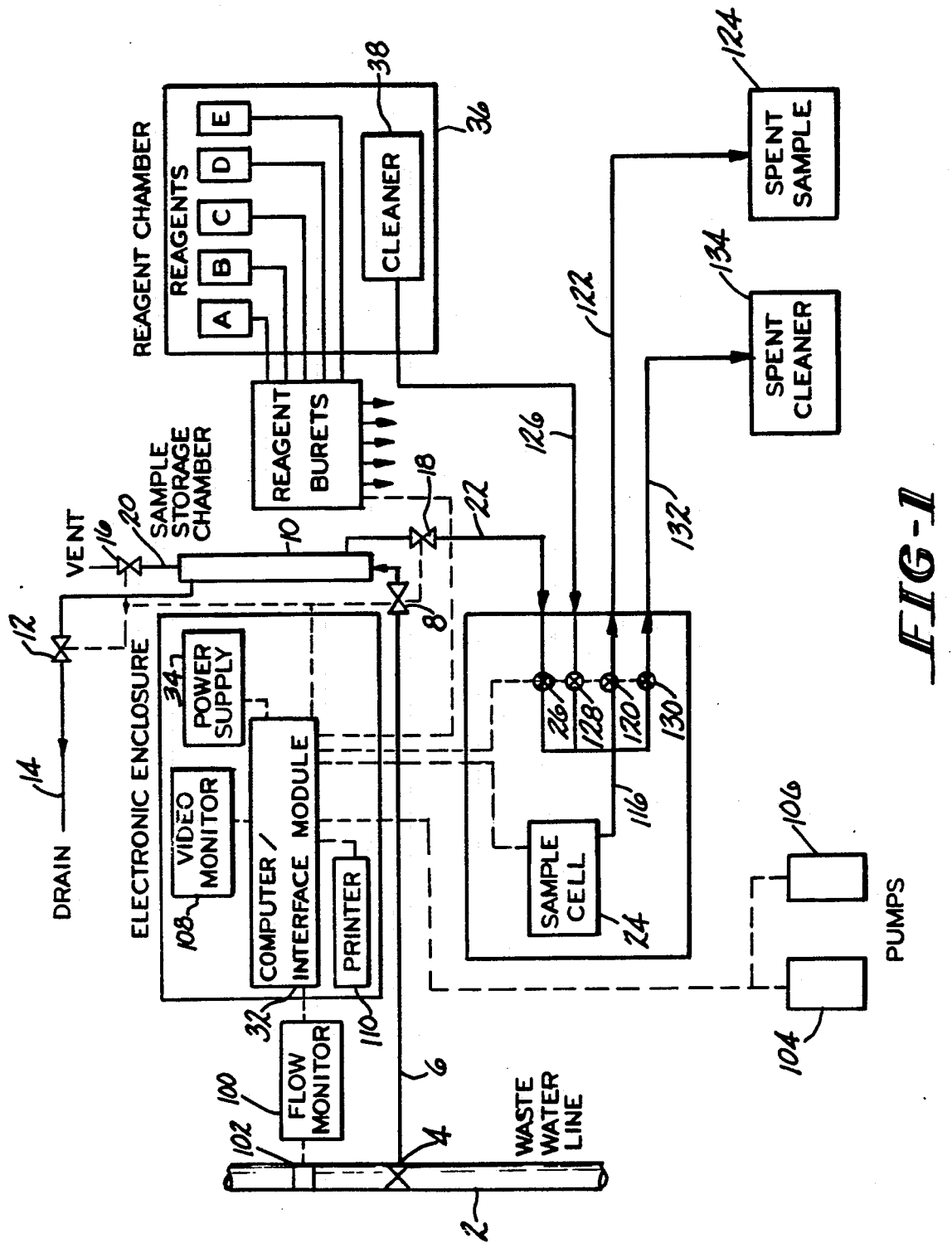
FIG. 1 represents a diagrammatic outline of the flow of materials and electrical output signals of a preferred embodiment of the present invention.

The present invention will be described in view of the preferred embodiment shown in FIGS. 1, 2, 3 and 4. FIG. 1 shows different components of this preferred embodiment and how they interact.

I. WATER SAMPLE INTRODUCTION

On the left side of FIG. 1, a waste water stream 2 is shown. This waste water stream contains reduced sulfur species (the aggregate thereof is known and referred to herein as Total Reducers or T.R.). An untreated sample of the stream 2 is drawn off at point 4 through sampling line 6 and an open solenoid valve 8 to sample storage chamber 10. The chamber is preferably a cylinder about two feet in height and one or two inches in diameter. The sample line 6 and sample chamber 10 are preferably flushed with a fresh waste water sample before each analysis through open solenoid valve 12 and drain line 14 to the drain for a short period of time (i.e. about 1 to 5 minutes) to insure that a representative fresh sample will be tested. The flow of the water sample through sampling line 6, chamber 10 and drain line 14 is under the positive pressure of the waste water stream 2. At the end of this flushing period, solenoid valves 8 and 12 close and trap a water sample in chamber 10. In the next few minutes after these valves close, any volatile oil or light hydrocarbons in the trapped sample float to the top of chamber 10 and any suspended solids drop to the bottom of chamber 10. Next, solenoid valves 16 and 18 open. Solenoid valve 16, located at the top of chamber 10, thus opens the chamber to the atmosphere through vent line 20 to vent and to facilitate the gravity draining of chamber 10. Solenoid valve 18 is located on line 22, which is a few inches above the bottom of the chamber 10. Thus, suspended solids in the sample will settle below the location of the inlet to line 22. When solenoid valves 16 and 18 are opened, the decanted water sample flows by gravity from chamber 10 to a sample cell 24 through line 22. The size of sample storage chamber 10 is relatively larger than the amount of the water sample to be sent to sample cell 24 and, accordingly, the volatile-rich upper portion of the trapped water sample in chamber 10 is excluded from the transferred sample. This feature of the present invention thus minimizes the chances of fouling problems caused by the presence of oil and/or suspended solids that may be present in the water sample.

Figure 3:
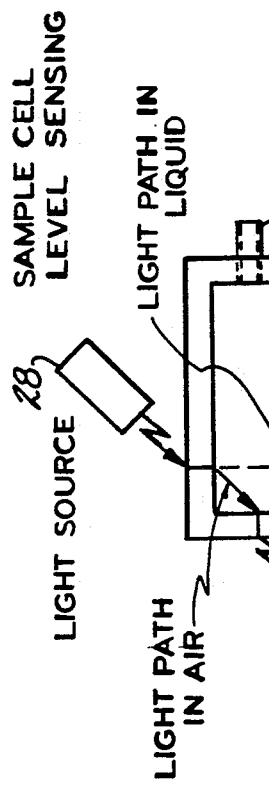
FIG. 3 are diagrammatic top and side views of the optical liquid level sensing system in the sample cell of the preferred embodiment of FIG. 1.
Figure 3:
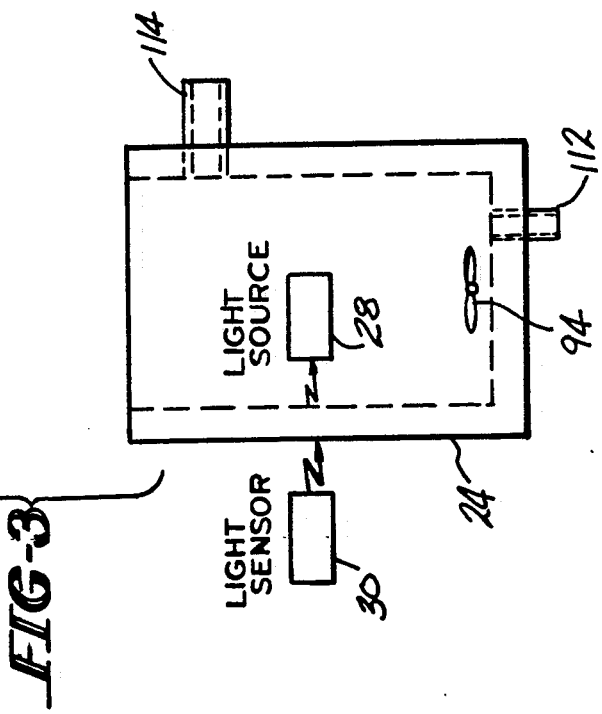

The amount of sample (preferably 100 ml of water sample) sent to sample cell 24 is controlled by an optical liquid level detector system shown in FIG. 3. The sample cell 24 is preferably made of clear acrylic plastic. Other similar clear, rigid and chemically inert materials may be used instead for constructing cell 24. As the sample cell 24 fills with the water sample from the bottom of the cell 24, it reaches the level of a light source 28 and light sensor 30. In an empty sample cell 24, the path of light from light source 28 passes through air directly to light sensor 30. When water reaches this level of the light path, the light path is refracted by the water away from the sensor 30. Both of the effects are shown in FIG. 3. At that point of time, the sensor 30 immediately sends an electronic signal to computer/interface module 32 in an electronic enclosure shown in FIG. 1. The computer/interface module 32 in turn sends an electronic signal to solenoid-activated piston 26 to close it, as it had previously done to open or close valves 8, 12, 16 and 18 as described above. Power supply means 34 provides the electric power for these signals. When solenoid-activated piston 26 closes, a precise predetermined sample quantity has been introduced into sample cell 24 and is ready for testing.

II. CHEMICAL REAGENT DISPENSING

The next step is the dispensing of four initial chemical reagents into the sample cell 24. These reagents are the same as used in the above-described Olin Water Services Analytical Method and consist of the following:

Reagent A. pH 5.0–5.5 phosphate buffer solution
  (VWR Scientific AL14180-4)
Reagent B. Methyl Red Indicator Solution (Optional)
  (Taylor Chemicals, Inc. R-1003F)
Reagent C. Hydrochloric Acid-6Normal (Optional)
  (Hach Company #884-49)
Reagent D. Starch Indicator Solution
  (Hach Company #349-37)

The reagent storage chamber 36 is shown in the upper right corner of FIG. 1. In this storage chamber 36, the bulk containers of the reagents A–D are stored as well as iodine titration solution (Reagent E) and cleaning solution storage container 38. The use of the latter two chemical solutions will be explained below. The bulk reagent containers A–E are connected to their corresponding reagent burets which are shown in detail in FIG. 2. The bulk storage containers A–E in chamber 36 preferably contain bulk supplies of each Reagent A–E to allow for at least 30 days of testing without the operator having to refill. The burets and their connecting means to the sample cell 24 are not shown in FIG. 1.

Figure 2:
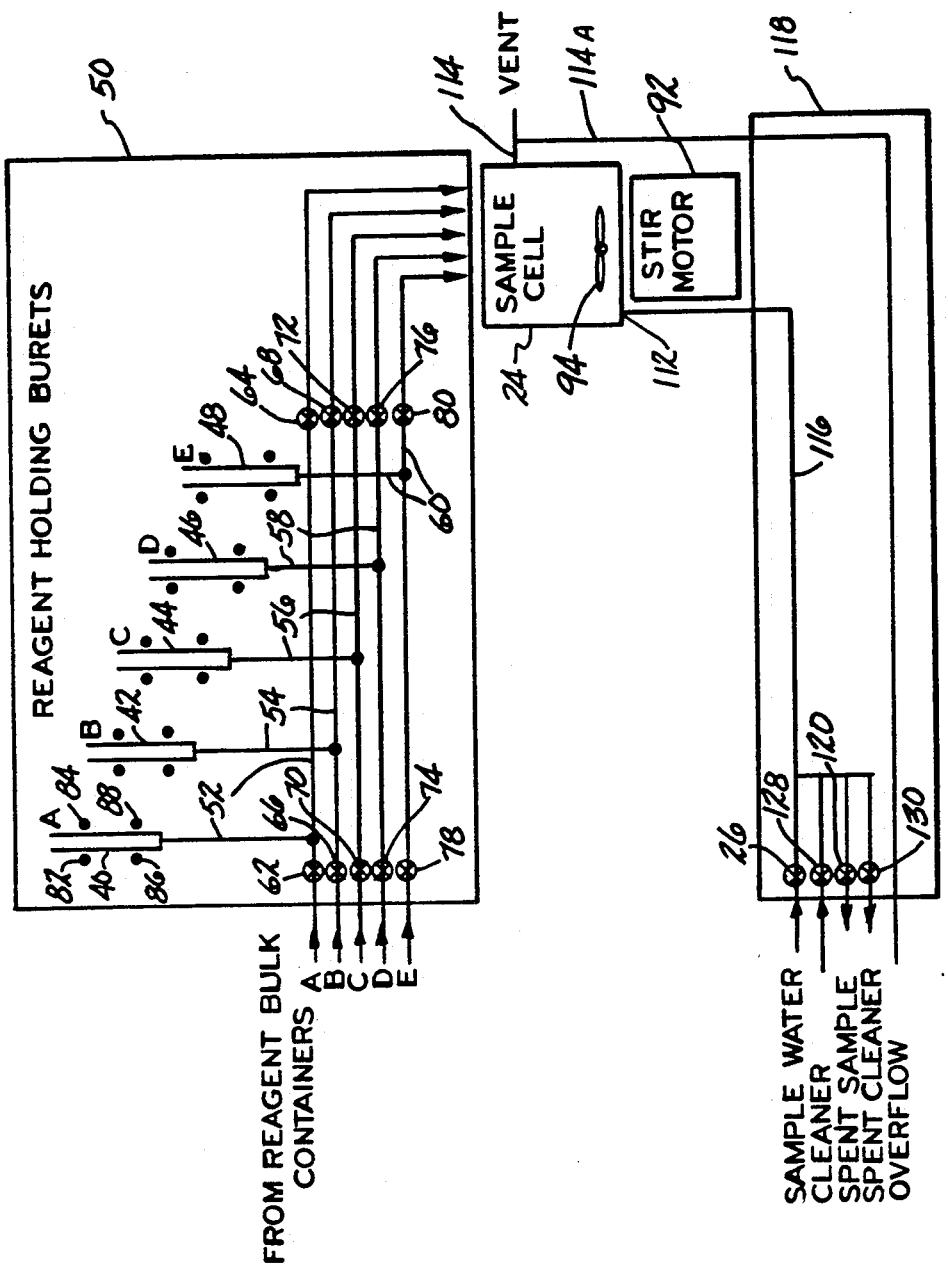
FIG. 2 is a detailed diagram of the dispensing means for the chemical reagents in the preferred embodiment shown in FIG. 1.

Now referring to FIG. 2, the individual reagents A–E are introduced into reagent holding burets 40, 42, 44, 46, 48, respectively, through top manifold 50 which contains combination feed/drain lines 52, 54, 56, 58 and 60. Located on each of these combination feed/drain lines are a pair of solenoid-activated pistons. Line 52 has fill pistons 62 and drain piston 64. Line 54 has fill piston 66 and drain piston 68. Line 56 has fill piston 70 and drain piston 72. Line 58 has fill piston 74 and drain piston 76. Line 60 has fill piston 78 and drain piston 80.

The reagent burets are each attached through their bottoms into top manifold 50. The combination feed/drain lines are machined channels in top manifold 50. Located adjacent to these machined channels is a sheet of flexible diaphragm material (not shown in FIG. 2). This diaphragm material is sandwiched between this top channeled plastic plate having the feed/drain lines and a solid bottom plastic plate. The end of each of the pistons is adhered to the diaphragm material and normally seal the feed/drain channels by spring means. When a solenoid is activated by computer/interface module 32, the corresponding piston is drawn back into the solenoid coil and the diaphragm in turn is drawn back to open the channel. When the solenoid is deactivated for a piston, a return spring on the piston is released and pushes the piston out of the solenoid coil and thereby pushes the diaphragm into a channel and closes it. This stops the flow of that reagent.

Reagent burets 40, 42, 44, 46 and 48 are all standard glass tube type burets. Preferably, burets 40, 42, 44 and 46 are identical in size (most preferably, a 0.25 inch inside diameter by 5.5 inches long). The buret 48 is preferably larger (most preferably a 0.75 inch inside diameter by 5.5 inches long). Of course, other buret diameters and lengths could be used and their preferred material of construction could be any other similar chemically inert and transparent material. The preferred diaphragm material is a sheet of a terpolymer elastomer made from ethylene-propylene diene monomer (EPDM). Other suitable chemically inert and flexible materials may be used instead.

To illustrate the operation of this reagent dispensing system, note in FIG. 2 that Reagent A flows by gravity from its bulk container in reagent chamber 36 to buret 40 through fill line 52 when solenoid-activated fill piston 62 is activated (opened) by an electronic signal from computer/interface module 32. This flow fills buret 40 upward from the bottom. The buret 40 is filled up to an upper optical liquid level system consisting of a pinpoint light source 82 and light sensor 84. This optical liquid level sensing system operates on the same principal as the above-discussed sample cell filling optical system, that is, immediately upon reaching this light level, a signal is sent to computer/interface module 32, which immediately sends an electronic signal to deactivate fill solenoid-activated piston 62 and thus closes the fill line channel and thus cut off the flow of Reagent A into the buret 40.

After this filling operation is completed, a controlled amount of Reagent A is tranferred from buret 40 to sample cell 24 by gravity through drain line channel 52 by activating (opening) solenoid-activated piston 64. Whereas the sample water enters cell 24 through hole 112, the Reagents A–E enter the cell from its open top which is in communication with the ends of the channels in top manifold 50. The amount of Reagent A sent to sample cell 24 is controlled by computer/interface module 32 which sends electronic signals to piston 64 to open and close based on a calibrated time period. Reagents B, C and D are added sequentially to their respective burets and then into sample cell 24 in the same manner. The preferred amounts and most preferred amount of each Reagent added to sample cell 24, when a 100 ml water sample having a pH between about 6 and 8 is being tested, are as follows:

| Reagent | Preferred Amounts | Most Preferred Amount |
| --- | --- | --- |
| A. pH 5.0–5.5 phosphate buffer | 0.5–5.0 ml | 1.0 ml |
| B. Methyl Red Indicator | 0–0.4 ml | 0.2 ml |
| C. HCl-6 Normal | 0–0.2 ml | 0.1 ml |
| D. Starch Indicator Solution | 0.75–2.0 ml | 1.0 ml |

The time period which determines each reagent addition is calibrated periodically (preferably, at least once per 24 hours) and is illustrated by the following procedure:

(i) Reagent A is filled into buret 40 to the level where the top light source 82 and light sensor 84 are;

(ii) Reagent A is then drained from buret 40 down to the lower optical liquid level system consisting of light source 86 and light sensor 88;

(iii) The time required to go from the upper to lower optical liquid level systems in buret 40 is measured and then stored in computer/interface module 32;

(iv) Since the volume of Reagent A between these two optical systems may be predetermined, volume increments of this Reagent A can be sent to sample cell 24 by merely programming the desired dispensing time in computer/interface module 32.

The amounts of the other Reagents B-E are calibrated in the same manner.

Before Reagents A, B, C and D are added to sample cell 24, a magnetic stirrer motor 92 (shown in FIG. 2) below cell 24 is energized to rotate magnetic stirrer bar 94 to provide agitation to the mixture of the water sample and Reagents. The stirrer bar 94 continues to rotate during titration of Reagent E into sample cell 24. The starting and stopping of the magnetic stirrer motor is controlled preferably by programmed computer sequencing in computer/interface module 32.

The Reagent autodispensing system, by using the above level sensing optics and the computer/interface module 32, may be programmed to automatically dispense each Reagent and self-calibrate itself to insure accuracy in adding the correct amount of each Reagent to the sample cell 24.

Furthermore, this autodispensing system does not employ peristaltic pumps to transfer these Reagents into the sample cell 24. Peristaltic pumps require frequent tubing changes (generally, at least monthly) to avoid leakage due to tubing wear. This continuous maintenance is expensive and time-consuming and, if inadvertently neglected, may cause serious damage or expense to the process being treated. In contrast, with the autodispensing system of the present invention, corrosion and leaks are minimized or practically eliminated because the diaphragm is the only moving part which the Reagents contact before they enter sample cell 24.

III. INITIAL LIGHT INTENSITY ADJUSTMENT

Figure 4:
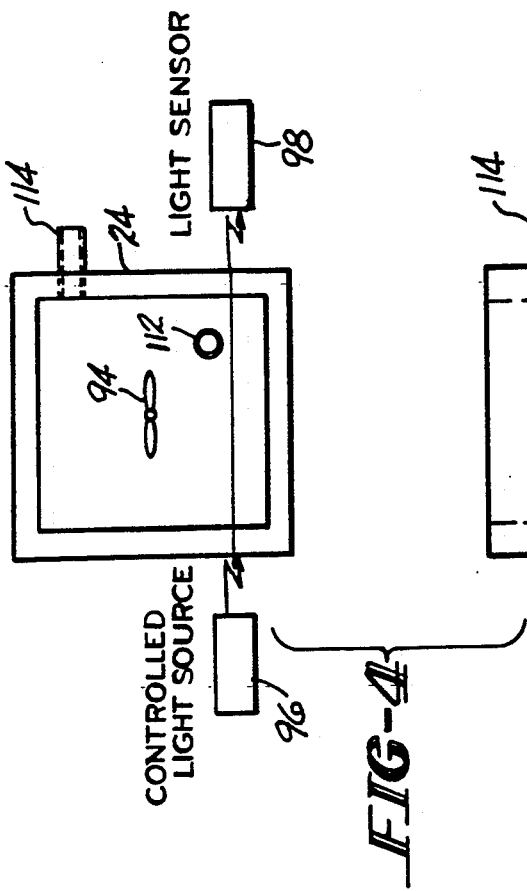
FIG. 4 are diagrammatic top and side views of the optical color change detection system in the sample cell of the preferred embodiment of FIG. 1.
Figure 4:
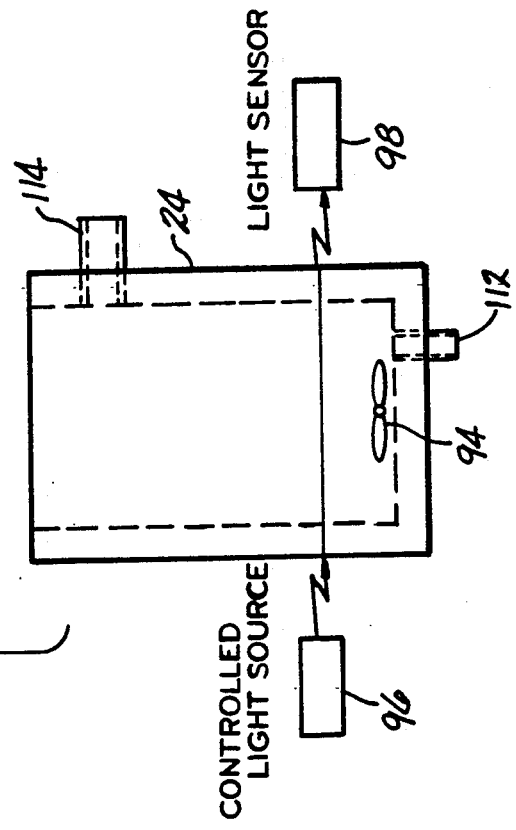

After the sample cell 24 has been filled with the water sample and Reagents A, B, C and D and the resulting mixture agitated, a second optical system placed on the cell 24 is activated. This second optics system is shown in FIG. 4 and preferably consists of a controlled light source 96 and a light sensor 98. Controlled light source 96 is preferably a red light-emitting diode having a light wavelength in the range of about 700 to 800 nanometers (nm).

The second optics systems is activated as follows: The light intensity of controlled light source 96 is gradually increased from zero intensity in increments by electronic signals from computer/interface module 32 until light sensor 98 senses the presence of the red light from the source 96 through the filled sample cell 24. At that point, sensor 98 sends computer/interface module 32 an electronic signal and the computer/interface module 32 stops ramping up the light intensity. The purpose of this initial adjustment of light intensity is to null out the interfering effects of sample color or turbidity which may vary from water sample to water sample.

IV. IODINE SOLUTION TITRATION

As soon as this light sensor 98 senses the light from source 96, an electronic signal is sent through computer/interface module 32 which activates drain piston 80 in order to start titrating Reagent E (the iodine solution). The preferred standard iodine solution is 0.025 Normal (Taylor Chemicals Inc. #R-0635-40F). Simultaneously, the computer/interface module 32 activates an on board precise time measuring means (preferably accurate within a 1/100 of a second) to measure the time period from when the iodine titration begins until an abrupt change in light transmission is detected by this second optics system. In particular, as the iodine is added, it preferably is reacted or consumed with the total reducer constituents in the sample. When these total reducers have completely reacted with the iodine solution, the starch indicator absorbs the excess iodine solution being titrated into cell 24. At this point, the whole sample/reagent mixture turns color (e.g. from a red to a blue). This end point color change is registered by the second optic system whereby light sensor 98 can no longer sense the controlled light from source 96. The controlled light beam is now absorbed in the sample mixture rather than passing through to sensor 98. When the end point is sensed, a signal is sent to computer/interface module 32 and solenoid-activated piston 80 immediately stops the iodine titrant flow and stops the on board electronic time measuring means which was started when titrant flow started.

V. TRANSLATION OF RESULTS AND SIGNAL OUTPUTS

As stated above, the time required to reach this end point is measured by the on board time measuring means in the computer/interface module 32. This measured time period is translated into a concentration of total reducers in the sample. This is done in the computer/interface module 32 by comparing the measured iodine titration time to the calibrated time versus volume factor stored in the computer/interface module 32 for buret 48. This comparison provides the total volume of iodine solution consumed by the sample being tested. From this determined iodine solution volume, the total reducers concentration in the sample (if thiosulfate is the primary total reducer constituent) may be calculated using the following Equation (A) which is stored in the computer/interface module 32:

$$\text{Total Reducers Concentration (measured in mg thiosulfate as sulfur per liter of water)} = \frac{A \times N \times (64.12) \times (1000 \text{ ml/l})}{V} \quad (A)$$

where
A = millileter iodine titrant
N = normality of the iodine titrant
V = volume of sample (in ml)
64.12 = 2 times molecular weight of sulfur Accordingly, if the normality of the iodine titrant is 0.025N and the amount of the sample used is 100 ml, then Equation (A) is:

Total reducers as $S^=$ (ppm) =

$$\frac{A \times 0.025 \times 64.12 \times 1000}{100} = A \times 16.03$$

After the computer/interface module 32 has calculated this total reducers concentration in the sample, the computer/interface module 32 further calculates the amount of a particular oxidant chemical needed to treat the total reducers in the water medium from which the sample was obtained. This calculation involved the following Equation (B):

$$\text{Oxidant Chemical To Be Added} = \text{Total Reducers Concentration (mg/l)} \times \text{Flow Rate of Water Medium} \times \text{Reaction Ratio of Total Reducers to Oxidant Chemical} \quad (B)$$

The flow rate of the water medium may be continuously measured by a flow monitor 100 which is attached to a water stream 2 at point 102 as shown in FIG. 1. The flow monitor 100 sends electronic signals (either intermittently or continuously) to computer/interface module 32. This flow rate signal is processed by the computer/interface module 32. Preferably, a continuous flow rate signal is received by the computer/interface module 32 from flow rate monitor 100. This continuously received (although possibly varying) input signals are used by computer/interface module 32 to calculate the output adjustment signal to the oxidant feed pumps 104 and 106 in accordance with above Equation (B). One or more oxidant feed pumps may be controlled by this computer output signal. The Reaction Ratio in the above Equation (B) is an empirical, programmable number dependent upon several factors including the type of specific oxidant used; the individual total reducer constituents present; type of oxidant; absence or presence of an oxidant catalyst; retention or reaction time; and starting concentration versus the desired final concentration of total reducers in the water medium. When copper sulfate catalyzed hydrogen peroxide is used as an oxidant, the main total reducer constituent is sodium thiosulfate, maximum retention time is about 0.75 hours and the concentration of total reducer concentration is desired to be lowered from about 200-400 mg thiosulfate as sulfur per liter of sample down to a desired level of less than 50 mg thiosulfate as sulfur per liter, this reaction ratio number programmed into computer/interface module 32 is is in the range of 1.5-2.5. However, the reaction ratio will vary with other oxidants and the presence of other primary total reducer constituents and where other ranges of starting and desired ending total reducer values are involved. Accordingly, the Reaction Ratio will vary from installation to installation and will have to be determined empirically in each case.

This calculated oxidant chemical amount to be added to the water medium is translated by computer/interface module 32 into a pump adjustment output signal which tells pumps 104 and 106 the quantity of oxidant to feed into the water medium. This pump adjustment output signal is preferably sent out from computer/interface module 32 to pumps 104 and 106 on a continuous basis. Thus, the pumps will be constantly adjusting the amount of oxidant chemical feed into waste water stream 2 in accordance with similar changes in flow rate input. After each total reducer sampling test, the total reducer value for Equation (B) will be updated and the pump adjustment output signal will be based on this new total reducer value until the next sampling test.

Alternatively or simultaneously with this process adjustment function, the system of the present invention may be used to monitor the total reducers concentration and, optionally, the flow rate in the water medium, as well as the amount of oxidant to be added. This monitoring function may be carried out by sending electronic output signals to a video monitor 108, printer 100 or a recorder (not shown in FIG. 1). Therefore, by this monitoring function, an operator may make a permanent record of the total reducers concentration in the water medium. Preferably, such monitoring means would log the flow rate information, the date and time of each Total Reducer analysis, the determined total reducer value, as well as the magnitude of the pump adjustment output signal sent to each pump. Moreover, it is desirable that computer/interface module 32 have the ability to store certain quantities of such data and having that stored data retrievable in both video and printout form. Furthermore, the operator, by only using the monitoring function, may manually control oxidant feed pumps 104 and 106 or additional standby pumps.

It should also be noted that if the water medium being sampled, and either adjusted or simply monitored for total reducer values, or both, is a static body of water rather than a flowing stream, then Equation (B) will have to be changed. The volume of water being treated will have to be used rather than the flow rate.

VI. WATER SAMPLE DRAINING

After the iodine titration is completed (i.e. color change end point registered), the agitation is stopped (i.e. the magnetic stirrer is turned off) and the liquid sample mixture is drained from sample cell 24 through drain opening 112 (shown in FIGS. 2, 3 and 4). Sample cell 24 is also preferably equipped with a vent opening 114 which facilitates the gravity draining of the cell. The draining system is best shown in FIG. 2. After exiting through drain opening 112, the drained sample enters drain channel 116 in bottom manifold 118 when solenoid-activated piston 120 is activated (opened). This bottom manifold 118 is constructed in a manner similar to top manifold 50. The preferred material for the channeled top plate and solid bottom plate of top manifolds 50 and 118 is acrylic plastic like cell 24. The solenoid-activated piston 120 is adhered to a flexible diaphragm material so that when it is activated, it causes an opening in drain channel 116 in the bottom manifold 118. Then, the drained sample exits manifold 118 by drain line 122 into spent sample container 124 (as shown in FIG. 1).

VII. CELL CLEANING CYCLE

After the sample cell 24 has been drained, the cell is filled with a cleaner solution made up of an appropriate hydrocarbon or halocarbon solvent. The cleaner solution is used to remove any residue contaminants (e.g. oil films and remaining total reducers) in sample cell 24 so that the next testing will be accurate. The cleaner solution is stored in cleaner reservoir 38 in reagent chamber 36. The cleaner solution flows by gravity through feed line 126 through solenoid-activated piston 128 into channel 116 in bottom manifold 118. It then enters sample cell 24 through opening 112 and fills the cell 24 from the bottom. Piston 128 is automatically opened as piston 120 is closed. A 150 ml aliquot of cleaner solution is added and piston 128 is then closed. This amount of cleaning solution added to sample cell 24 is controlled by the same liquid leveling sensing system 28 and 30 used to add the sample water to the cell 24. In this case, there is a time delay between when the cleaning solution level passes the leveling sensing system and when piston 128 is closed. If too much cleaner is added, the excess will exit sample cell 24 by exit vent 114 and overflow line 114A. After the cell is filled with cleaner, the magnetic stirrer motor 92 is energized to start magnetic stirrer bar 94 to improve the cleaning action. The cleaning operation lasts from about 1 to 5 minutes. The stirrer motor 92 is stopped and the cleaning solution is drained by gravity from cell 24 through drain opening 112, channel 116, and through piston 130, which operates in the same manner as the other solenoid-activated pistons. After passing by piston 130, the spent cleaner solution flows through line 132 into spent cleaner container 134 (shown in FIG. 1). The spent cleaner solution may be recycled or discarded.

VIII. FLUSHING CYCLE

After the above cleaning cycle is completed, the sample cell is flushed with sample water or fresh water through line 22, solenoid-activated piston 26, channel 116 into cell 24. Again, the liquid leveling system 28 and 30 is used to obtain the desired amount of flush water. The magnetic agitator mechanism restarts as described previously and flush water is agitated in the cell 24 for a predetermined time interval (e.g. from about 1 to about 5 minutes) and then drained through channel 116 and piston 120 back to the spent sample container 124.

The cell is ready for the next test cycle. Under normal operation, a sample may be taken once per hour. If the output signal indicates an uncharacteristic high or low (outside a predetermined percentage of change) total concentration of total reducer constituents, the testing frequency may be automatically increased (e.g. three times per hour) until the measured concentration appears stabilized.

IX. COMPUTER COMMAND SEQUENCE SUMMARY

Computer/interface module 32 is preferably made up of an eight BIT computer (with a keyboard) which is in combination with an interface module package capable of directing the computer commands to the individual items (e.g. solenoids, solenoid-activated pistons, pumps and magnetic agitator system) to be controlled in sequence. The preferred interface module contains four computer programmable interface adapter integrated circuits. These four integrated circuits route the computer commands to the electronic circuits and items that are to respond to these commands. Of these four integrated circuits, one integrated circuit preferably controls the solenoid-activated pistons that start and stop the liquid flow into and out of sample cell 24. The second controls the liquid level in the reagent holding burets by responding to the light sensors attached to these burets. The second also controls the liquid level in sample cell 24 by responding to the level sensor in that sample cell. The third controls the milliamp level that is sent out to modulate the chemical oxidant feed (e.g. process adjustment pumps) and the intensity of the light source 96 used to determine titration time in sample cell 24. The fourth integrated circuit controls the voltage level which is compared to the flow monitor input milliamp signal and the relay drives for the solenoid valves which open and close the sample storage chamber 10.

The computer/interface module 32 also preferably contains integrated circuits and other means which convert digital electronic signals into analog electronic signals and vice versa.

The above described preferred embodiment of the process and apparatus of the present invention is directed by the following sequence of computer operations:

1. The computer checks its internal day time clock and checks to see if it is test time.

2. At test time the test sequence is started and performed as follows:

(a) Flush and capture a new test sample into the sample storage chamber 10.

(b) Wait a predetermined programmed time period to allow for separation of suspended solids and oil in chamber 10.

(c) Fill the sample cell 24 with 100 mls of sample water from the sample storage chamber 10.

(d) Turn on the magnet stirrer 94.

(e) Inject Reagents A-D into burets and then into cell 24.

(f) Set light intensity in light source 96 to compensate for color and turbidity.

(g) Inject iodine solution into buret 48 and then cell 24 by time/volume means until the color change end point is detected.

(h) Convert the time to titrate to volume of iodine used.

(i) Calculate the total reducer value.

(j) Measure the rate of flow in the waste water stream from the flow monitor 100.

(k) Calculate the oxidant pump rate required based on total reducer value calculated in (i), reaction ratio and measured water stream flow rate of (j).

(l) Send the pump setting output signal to the pumps 104 and 106 corresponding to the calculated oxidant pump rate of (k).

(m) Drain the spent sample from the sample cell to the spent sample storage container 124.

(n) Fill the sample cell 24 with up to 150 ml of cleaning solution.

(o) Agitate the cleaning solution for programmed time period to clean the sample cell for the next test.

(p) Drain the cleaning solution from the sample cell to the spent cleaner container 134.

(q) Fill sample cell 24 with up to 150 ml of fresh water or sample water to flush cell 24 for next test (r) Agitate flushing solution for programmed time period.

(s) Drain the flushing solution from the sample cell to spent sample container 124.

(t) Print the time, date, total reducer value, pump rates and flow rate on the printer 110 and show on the video monitor 108.

3. While waiting for the next total reducers test, the computer 32 continues to monitor the flow rate of the waste water stream and updates the pump setting output signal (1) above based on the last total reducer value, predetermined reaction ratio and continuously measured flow rate. This pump setting output signal calculated in (u) above is continuously sent to pumps 104 and 106 and the data in (t), above, is updated and printed at printer 110 and video monitor 108.

What is claimed is:

1. A process for monitoring or adjusting, or concentration of total reducer constituents in an aqueous medium, comprising the steps of:

(1) adding a predetermined aliquot of said total reducers-containing water to a sample cell, said sample cell equipped with means for transmitting light of variable intensity through the filled sample cell and means for sensing the presence or absence of said light transmission after passing through said filled sample cell;

(2) adding to said aliquot-filled sample cell predetermined amounts of a pH 5.0-5.5 buffer reagent, an optional methyl red indicator, an optional hydrochloric acid solution and a starch indicator;

(3) activating said light transmission means in said sample cell in order to send light of a sufficient intensity through said filled sample cell to be sensed by said light sensing means;

(4) then titrating an iodine solution into said filled sample cell at a predetermined rate of addition while sensing the presence or absence of said light transmission in said cell;

(5) measuring the time taken from the start of the iodine titration until the absence of said light sensing through said filled cell is detected;

(6) translating this time measurement into either the concentration of total reducer constituents in said water medium or into the amount of an oxidant chemical to be fed into said water medium, or both; and (7) based on said translation, sending either a first output signal to at least one monitoring means or a second output signal to at least one process adjustment means location whereby said concentration of total reducer constituents in said water medium is adjusted, or sending both first and second signals.

2. The process of claim 1 wherein said sample water has a pH of about 6 to about 8, for each 100 ml aliquot of sample water added to said sample cell, the following amounts of chemicals are added to said sample cell:

| | |
|---|---|
| A. pH 5.0–5.5 Phosphate Buffer | 0.5–5.0 ml |
| B. Methyl Red Indicator | 0–0.4 ml |
| C. HCl (6 Normal) | 0–0.2 ml |
| D. Starch Indicator Solution | 0.75–2.0 ml |

3. The process of claim 2 wherein said amount of chemicals added to said sample cell are:

| | |
|---|---|
| A. pH 5.0–5.5 Phosphate Buffer | 1.0 ml |
| B. Methyl Red Indicator | 0.2 ml |
| C. HCl (6 Normal) | 0.1 ml |
| D. Starch Indicator Solution | 1.0 ml |

4. The process of claim 2 wherein the normality of the iodine titrant is 0.025 Normal.

5. The process of claim 1 wherein the concentration of total reducer constituents in said water medium is about 200 to about 400 mg as sulfur ($S^=$) per liter of water.

6. The process of claim 5 wherein said process adjustment means is an oxidant feed pump and a sufficient amount of oxidant is added to said water medium to lower the concentration of total reducers to below about 50 mg as sulfur ($S^=$) per liter of water.

7. The process of claim 1 wherein said sample cell is cleaned with a cleaning solution between each total reducer measurement test.

8. The process of claim 1 wherein said sample cell is flushed with fresh water or sample water between total reducer measurement tests.

9. The process of claim 1 wherein said first output signal is sent to either a video monitor, a printer or both.

10. The process of claim 1 wherein said light transmission from said light transmission means to said light sensing means is at about 700 to about 800 nanometers.

* * * * *